(12) United States Patent
Lin

(10) Patent No.: US 6,907,883 B2
(45) Date of Patent: Jun. 21, 2005

(54) ELECTRIC CONDOM RING

(76) Inventor: Jerome Lin, 11F-1, No.2, Lane 391 Chung Cheng Road, Yung Ho City, Taipei Hsien (TW)

( * ) Notice: Subject to any disclaimer, the term of this patent is extended or adjusted under 35 U.S.C. 154(b) by 0 days.

(21) Appl. No.: 10/685,487

(22) Filed: Oct. 16, 2003

(65) Prior Publication Data

US 2005/0081863 A1  Apr. 21, 2005

(51) Int. Cl.[7] .............................................. A61F 6/04
(52) U.S. Cl. ....................................... 128/844; 128/842
(58) Field of Search .............................. 128/842, 844, 128/918

(56) References Cited

U.S. PATENT DOCUMENTS

| | | | | |
|---|---|---|---|---|
| 3,623,481 A | * | 11/1971 | Curran | 601/74 |
| 4,834,115 A | * | 5/1989 | Stewart | 128/842 |
| 5,377,692 A | * | 1/1995 | Pfeil | 128/844 |
| 5,573,499 A | * | 11/1996 | McAllister | 601/70 |
| 5,928,170 A | * | 7/1999 | Garrigan | 601/47 |
| 6,485,408 B2 | * | 11/2002 | Orten | 600/38 |
| D496,458 S | * | 9/2004 | Lin | D24/143 |

* cited by examiner

*Primary Examiner*—Henry Bennett
*Assistant Examiner*—Camtu Nguyen
(74) *Attorney, Agent, or Firm*—Bacon & Thomas PLLC

(57) ABSTRACT

A condom ring using a miniature vibrating motor, a battery, and a conductive spring plate cased in a vibrating device on the ring. A conductive spring plate which is connected to the battery on one end and crossing over the insulation plate, which free of connection with the motor on the other end. When pushing a rod at one end of the insulation plate inward, making the insulation plate out of touch with the conductive spring plate, the free end of the conductive spring plate becomes connected to the motor for turning on power supply and causing vibration. The ring can be put on the penis when in use or be used with a condom.

1 Claim, 3 Drawing Sheets

ELECTRIC CONDOM RING

BACKGROUND OF THE INVENTION

The present invention relates to an electric condom ring, particularly to a condom ring having a miniature vibrating motor and a battery to be used on a condom to enhance sexual pleasure.

In order to promote sexual safety in youth, the Center for Disease Control (CDC) of the Department of Health advocates the use of condom but to of a little result. The inventor therefore develops the electric condom ring device to provide people with a choice to have more fun and pleasure when using condom in their sex life.

SUMMARY OF THE INVENTION

The primary objective of the present invention is to provide an electric condom ring using a miniature vibrating motor, a battery, and a conductive spring plate cased in a vibrating device of the electric ring. A conductive spring plate which is connected to the battery on one end and crossing over the insulation plate, which free of connection with the motor on the other end. When pushing the rod at one end of the insulation plate inward, making the insulation plate out of touch with the conductive spring plate, the free end of the conductive spring plate becomes connected to the motor for power supply and vibrating to increase sexual enjoyment.

Another objective of the present invention is its independent use on a penis.

To enable a further understanding of the aforesaid objectives and the technological methods of the invention herein, the brief description of the drawings below is followed by the detailed description of the preferred embodiment.

BRIEF DESCRIPTION OF THE DRAWINGS

FIG. 3 shows a cross-sectional view according to the invention when turning on.

DETAILED DESCRIPTION OF THE PREFERRED EMBODIMENTS

To better understand the characteristics and novelties of the invention, descriptions shall be given with the accompanying drawings hereunder.

Figure 1:
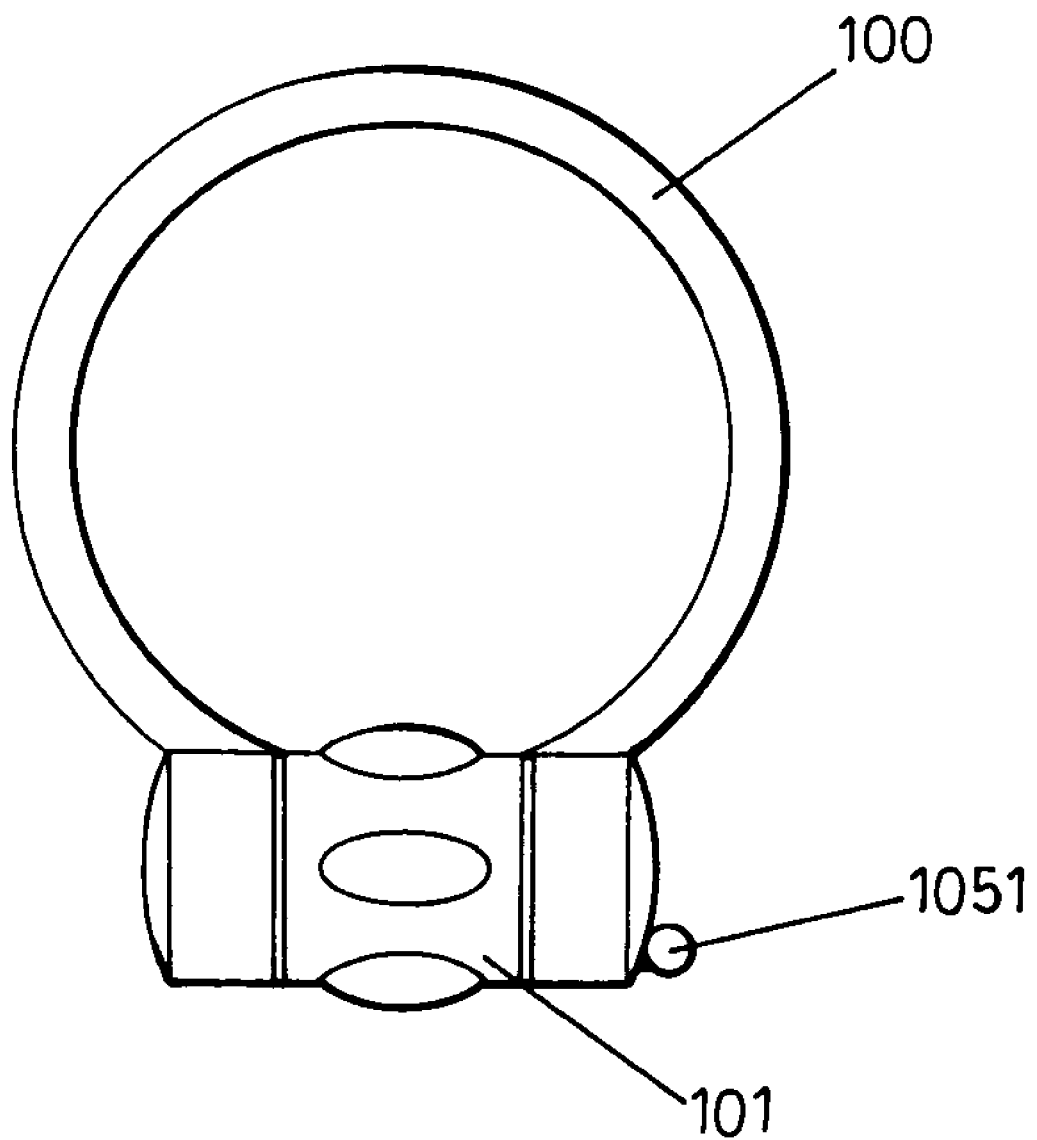
FIG. 1 shows a perspective schematic drawing of the invention.
Figure 2:
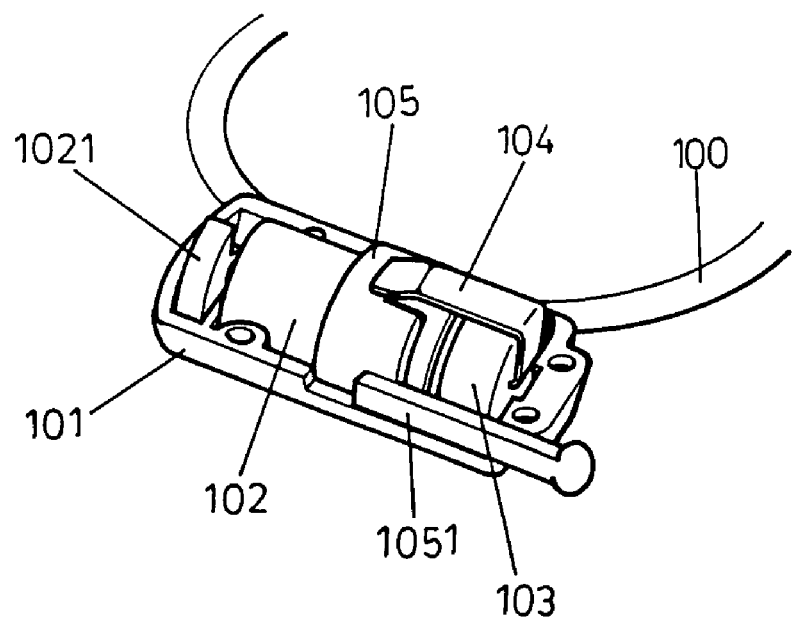
FIG. 2 shows a cross-sectional view according to the invention.
Figure 3:
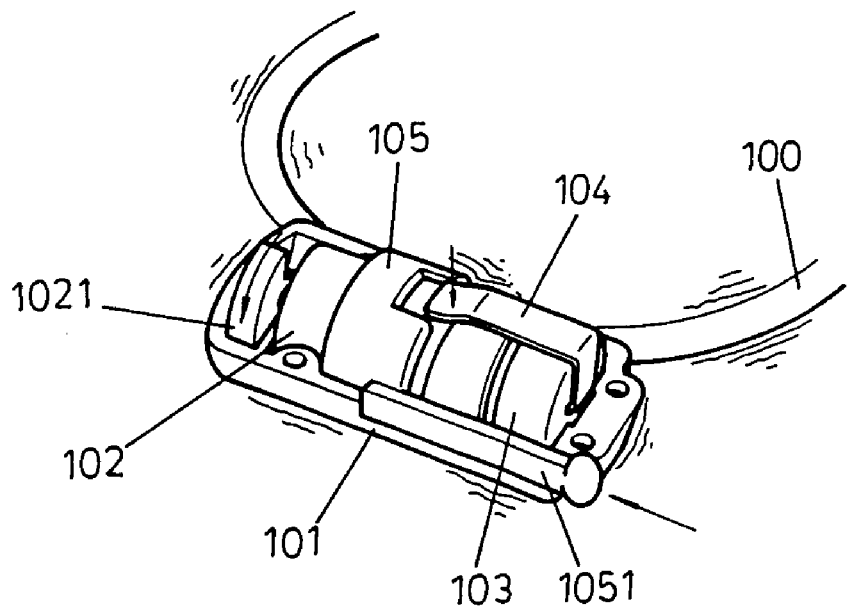

Referring to FIGS. 1–2, the invention provides a circular ring, wherein, a vibrating device (101) disposed on the ring houses a miniature vibrating motor (102), a battery (103), and a conductive spring plate (104). A rotator (1021) mounted at the front end of the motor (102) is eccentric providing vibration when rotating. The rear end of the motor (102) ("−" negative charge) is connected to a battery (103) ("+" positive charge). Referring to FIG. 2, a conductive spring plate (104) crossing over the insulation plate (105), which has not yet in connection with the motor (102). While the conductive spring plate (104) on the other end being connected to the "−" negative end of the battery (103). Referring to FIG. 3, when pushing the rod (1051) at one end of the insulation plate (105) inward, making the insulation plate (105) out of touch with the conductive spring plate (104) the conductive spring plate (104) becomes connected to the "+" positive end of the motor (102) making the electric ring (100) vibrate.

Figure 4:
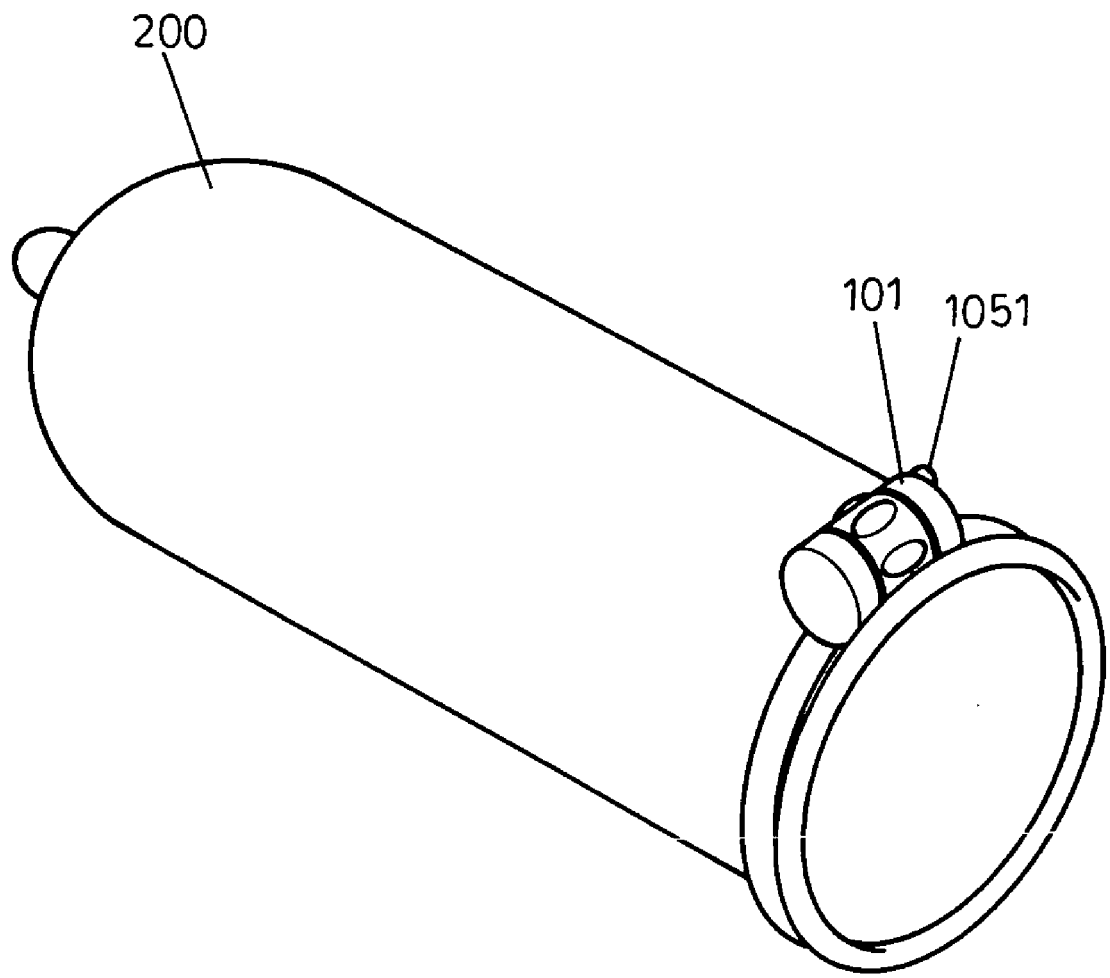
FIG. 4 shows the external view of the invention in use with a condom.

Normally, the electric ring can be used directly on the penis, or as shown in FIG. 4, the electric ring (100) can also be used with a condom.

In conclusion, the invention not only enhances sexual gratification but also increases the number of uses of a condom.

It is of course to be understood that the embodiment described herein is merely illustrative of the principles of the invention and that a wide variety of modifications thereto may be effected by persons skilled in the art without departing from the spirit and scope of the invention as set forth in the following claims.

What is claimed is:
1. An electric condom ring comprising:
 (a) a ring of sufficient diameter for encircling a condom worn by a user; and
 (b) a vibrating device mounted on the ring, the device including a battery, a motor powered by the battery and having a front end provided with an eccentric rotator and a rear end connected to the battery, a conductive spring plate including a first end for electrical connection with the motor and a second end connected to the battery, an insulation plate movable between a first position in which the first end of the spring plate is maintained out of electrical connection with the motor and a second position in which the first end of the spring plate is disposed in electrical connection with the motor, and a rod for operation by the user to move the insulation plate between the first and second positions.

* * * * *